United States Patent [19]

McGreevy et al.

[11] Patent Number: 4,690,684

[45] Date of Patent: Sep. 1, 1987

[54] MELTABLE STENT FOR ANASTOMOSIS

[75] Inventors: Francis T. McGreevy, Aurora; Karl W. Hahn, Englewood, both of Colo.

[73] Assignee: C. R. Bard, Inc., Murray Hill, N.J.

[21] Appl. No.: 754,472

[22] Filed: Jul. 12, 1985

[51] Int. Cl.$^4$ .......................... A61F 2/04; A61B 17/04
[52] U.S. Cl. ........................................ 623/12; 623/66; 128/334 R; 128/1 R
[58] Field of Search ............... 128/1 R, 334 R; 623/1, 623/12, 66

[56] References Cited

U.S. PATENT DOCUMENTS

| | | | |
|---|---|---|---|
| 1,470,707 | 11/1923 | Bates | 128/334 R |
| 3,683,926 | 8/1972 | Suzuki | 623/66 |
| 4,061,134 | 12/1977 | Samuels et al. | 623/1 X |
| 4,546,500 | 10/1985 | Bell | 623/1 |
| 4,563,779 | 1/1986 | Kelman | 128/334 R X |

Primary Examiner—Richard J. Apley
Assistant Examiner—Alan W. Cannon
Attorney, Agent, or Firm—John R. Ley

[57] ABSTRACT

A stent for the anastomosis of a vessel comprises an integral solid of biologically compatible material which is adapted to melt from a solid into a fluid in response to heat energy or body temperature into the fluid which flows through the vessel. Preferably the stent is formed of frozen material, and has a temperature which is substantially less than the temperature of the vessel upon insertion. Upon melting, the biologically compatible material naturally integrates with the fluid normally conducted by the vessel. The stent may be advantageously formed of frozen blood plasma or other blood fluid which is compatible with the blood normally conducted by an artery or a vein. When used in conjunction with thermal bonding techniques, the stent aligns the ends of the vessel for thermal bonding without the necessity for taking the time-consuming circumferentially-spaced stay sutures. The thermal mass and temperature of the stent protects the inner coating, the tuncia intima, from substantial damage from the heat applied during thermal bonding.

17 Claims, 2 Drawing Figures

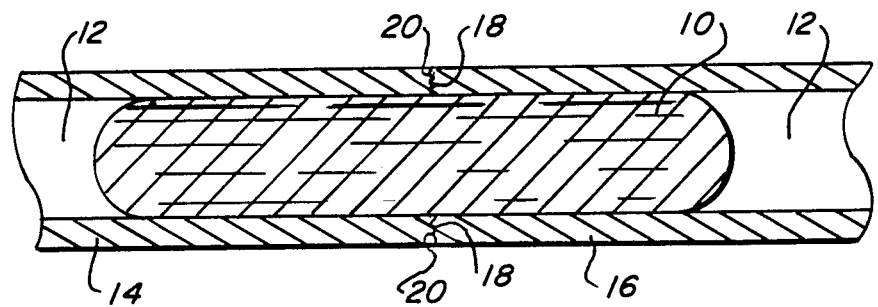
Fig_1
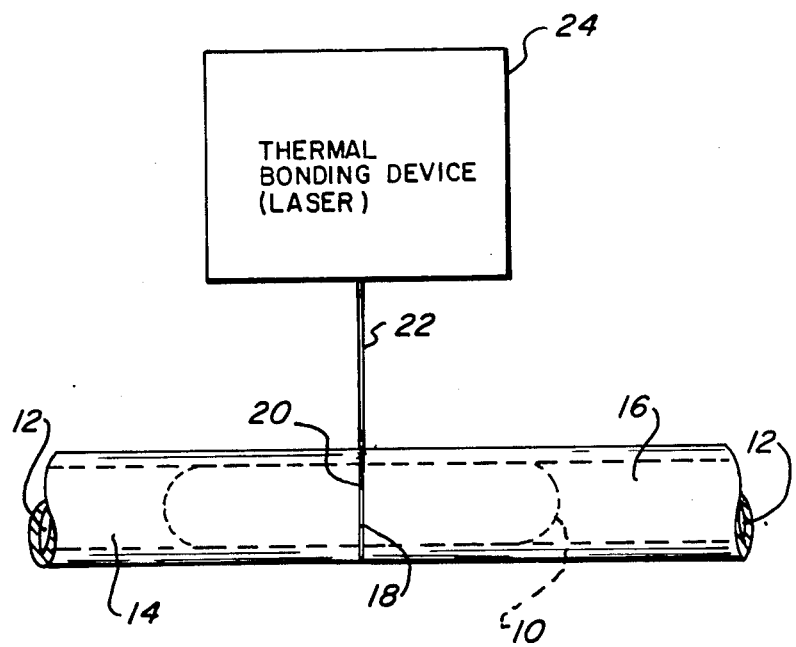
Fig_2

MELTABLE STENT FOR ANASTOMOSIS

This invention relates to the anastomosis of vessels, such as arteries, veins, vas deferens, or fallopian tubes. More particularly, the present invention relates to a surgical stent and a method of anastomosing vessels using a stent. The present invention is particularly useful in conjunction with thermal bonding techniques, e.g. lasers, for joining the ends of vessels during anastomosis.

BACKGROUND INFORMATION

The traditional surgical procedure for anastomosing the ends of a severed vessel has been a suturing operation. The ends of the vessel are stitched together while the fluid flow in the vessel is clamped off. Due to the relatively small size of the vessel and the relative difficulty in stitching around the circumference of the vessel, the traditional suturing technique is somewhat time-consuming. The vessel itself and the tissue supplied with fluid by the vessel can become damaged, due to the terminated flow of fluid while the vessel is clamped off, if the procedure becomes too time-consuming. Also, fluid sometimes leaks from the vessel where the sutures penetrate the vessel walls.

Various surgical prostheses and techniques have been devised to improve the ability to achieve successful anastomosis and to reduce the time consumed by the anastomosis procedure. Tubular prostheses have been inserted into the interior and over the exterior of the vessel which is anastomosed. Such prostheses aid in holding the vessel ends during the procedure and while the vessel tissue grows back together during healing. Some of the prostheses are made from biological material which is slowly absorbed by the body tissue as the healing progresses. The biological material is usually a chemical or solid material which dissolves slowly over a period of weeks by chemical or biological absorption. Other types of prostheses ar emade from permanent materials, such as plastics or metals, which remain permanently within the interior of the vessel after healing is completed. Other prostheses incorporate both permanent and biologically absorbable materials. As the biologically absorbable materials dissolve, they are replaced by natural tissue growth and the permanent materials are thus permanently incorporated into the living tissue.

The prostheses which are biologically dissolvable or absorbable are somtimes regarded as preferable, because no foreign object remains after the healing is completed. However, they also present disadvantages. Permanent prostheses can partially occlude a vessel and thereby permanently reduce the fluid flow therethrough. The living tissue may attempt to reject the foreign body of the prostheses. Unnatural tissue growth caused by adverse tissue reaction may fully or partially occlude the vessel. An additional surgical procedure is often required to remove the remaining permanent prostheses after anastomosis is complete, or if medical complications result from tissue rejection.

A relatively new procedure fro anastomosis involves completely bonding the ends of the vessel togehter, usually by a laser beam. Thermal bonding heats the ends of the vessel and creates an interlinked and cross-linked matrix of dessicated tissue fibers which hold the ends of the vessel together until natural tissue growth occurs. One advantage of thermal bonding is that a continuous bonded "seam" is created to obtain a more complete and leak-free jucntion of the vessel ends than is possible by using a number of spaced stitches in the traditional suturing operation. Thus, better anastomosis is possibly achieved by use of the thermal bonding technique.

One disadvantage of anastomosis by thermal bonding is that it requires about the same amount of time to complete as the more traditional anastomosis by use of the surgical suturing technique. Prior to thermal bonding by application of a laser beam or other thermal energy bonding beam, the vessel ends must be aligned, abutted and held together without the aid of metallic clamps or the like. Metallic clamps or the like would divert or deflect the energy beam and might cause undesirable localized heating and tissue destruction. To align and hold the vessel ends prior to application of the thermal bonding beam, three stay sutures or stitches are typically taken at 120° intervals around the circumference of the vessel. Inserting the three stay sutures consumes almost as much time as the traditional technique of completely suturing around the circumference of the vessel. The three stay sutures can also bend or otherwise influence the energy beam to create a somewhat uneven distribution or application of the energy beam to the vessel. The degree or density of tissue bonding may therefore be influenced from location to location around the circumference of the vessel. The stay sutures also pose some risk of being rejected by the tissue and, of course, the insertion of the sutures themselves requires the ends of the already damaged vessel to be pierced during stitching, which further damages the vessel and creates a possibility for fluid leakage.

GENERAL SUMMARY OF THE INVENTION

It is the objective of the present invention to provide a new and improved stent or prosthesis for use in anastomosis of vessels, and to teach a new and improved method of anastomosing a vessel, which achieve the following significant features, advantages and improvements:

reducing the amount of time consumed by the anastomosis surgical procedure, particularly a thermal bonding procedure, by eliminating the necessity for taking stay sutures to align the vessels prior to anastomosis;

achieving improved tissue bonding by more uniform and consistent energy beam distribution when thermally bonding the ends of the vessel, by eliminating the stay sutures;

avoiding the problems associated with adverse tissue reaction, tissue rejection of foreign substances and/or reduced fluid flow due to partial or full occlusion of the vessel;

eliminating the necessity for subsequent surgical procedures to remove the inserted prostheses after healing of the anastomosed vessel or as a result of tissue rejection; and protecting the important inner coat (tuncia intima) of the vessel from destruction due to heat applied during a thermal bonding procedure.

Generally summarized and in accordance with the foreging and other aspects, the present invention comprises a stent for insertion into the interior of the ends of a tubular vessel in a living being to align the ends of the vessel during anastomosis. The stent comprises an integral solid of biologically compatible material adapted to melt from a solid into a fluid. Melting occurs relatively rapidly and in response to heat energy, preferably natural body heat, after completion of the surgical procedure. When initially inserted, the stent has a temperature substantially less than the temperature of the vessel. The low temperature of the stent protects the inner coating or tuncia intima from heat damage during the thermal bonding procedure. The integral solid offers sufficient integrity during the bonding procedure to hold the vessel ends together in alignment until the anastomosis is completed. After completion of the bonding procedure, the biologically compatible material fully melts into the fluid conducted through the vessel. No occlusion or tissue rejection problems are created. Anastomosis by thermal bonding can be completed very rapidly without the necessity for taking the three stay sutures. Because of the absence of the stay sutures, the energy beam is uninfluenced and is more uniform in effect to achieve the improved bonding. The biologically compatible material may advantageously comprise solidified or frozen natural or synthetic fluid of the type which usually flows through the vessel. For example, the stent can be formed of frozen blood plasma which readily melts into the compatible blood in the artery or vein after anastomosis, thereby avoiding problems of tissue rejection or adverse tissue reaction. Alignment difficulties are avoided even when the stent is used in conjunction with a conventional anastomosis technique.

Generally summarized and in accordance with the foregoing and other aspects, the present invention also comprises a method of anastomosing a tubular vessel in a living being comprising the steps of inserting a stent having the characteristics described into the ends of the vessel, substantially abutting the ends of the vessel over the stent, and connecting the ends of the vessel by a surgical procedure prior to the integral solid stent melting within the interior of the anastomosed vessel. Preferably, the method of connecting the ends of the vessel is by thermal bonding. In order to maintain the integral solid of biologically compatible material within the interior of the vessel during anastomosis, the stent may be of a configuration which provides a sufficient thermal mass to prevent premature melting. The stent may therefore be of an initial size which substantially occludes the interior of the vessel until the surgical procedure is completed, but thereafter melts or rapidly dissolves to open the interior of the vessel to fluid flow.

The invention is more specifically defined by the following claims. A more complete understanding of the various aspects of the invention, and its improvements and advantages, can be obtained from the following description of a preferred embodiment of the invention taken in conjunction with the accompanying drawings.

BRIEF DESCRIPTION OF THE DRAWINGS

FIG. 1 is a sectioned side view of a part of a vessel having a stent according to the present invention inserted therein.

FIG. 2 is a generalized side view of a vessel being anastomosed by thermal bonding and by use of the stent shown in FIG. 1.

DESCRIPTION OF PREFERRED EMBODIMENTS

A stent according to the present invention is shown in FIG. 1 and is referenced 10. The stent 10 is shown inserte within the interior 12 of a vessel which is to be anastomosed. The vessel is defined by a vessel portion 14 and a vessel portion 16. The vessel portions 14 and 16 may be of the same vessel in the situation where the vessel has been severed. The vessel portion 14 may be from one vessel and the vessel portion 16 may be from another vessel, in those situations where two separate vessels are desired to be joined together. One of the vessel portions 14 or 16 could also be of an artificial or synthetic origin, and used to extend or otherwise connect to an existing human vessel portion.

The stent 10 initially has the configuration of an elongated body, such as an elongated cylinder. Approximately one-half of the stent is initially inserted into the interior 12 of one vessel portion, thereby leaving approximately the other half of the stent protruding away from the end of the one vessel portion. Thereafter, the other vessel portion to be joined is pulled or otherwise manipulated over the protruding portion of the stent. The two vessel portions are worked together on the stent until the end 18 of vessel portion 14 and the end 20 of vessel portion 16, are abutted together in an aligned relationship over the stent 10. In this manner the stent acts to align the vessel ends and hold them in an abutting relationship so that they may be joined together by a surgical technique.

The diameter or cross-sectional size of the stent 10 is such that it substantially fully occupies the interior 12 of the vessel portions 14 and 16 at the ends 18 and 20. The diameter or cross-sectional configuration of the stent may actually slightly expand the portions of the vessel adjoining the ends 18 and 20. By slightly expanding or fully occluding the interior of the vessel at the locations adjoining its ends, the vessel portions are held or retained on the stent. The solid integral structure of the stent and its retaining capabilities for the ends of the vessel portions provide a relationship substantial and rigid structure about which to facilitate and conduct the anastomosis.

The stent 10 is preferably formed as an integral solid of biologically compatible material, which fully melts from a solid into a fluid relatively quickly after completion of the surgical procedure in response to applied heat energy. As used herein the term "melts" or a formative thereof refers to a physical change from a solid or solid-like form to a fluid (liquid or gas) form. Melting will normally occur in response to the application of heat energy or energy creating heat. Usually sufficient heat energy for melting is available from natural body heat, but in some instances sources of radiated energy capable of creating localized heat, such as microwave energy, might be externally applied to complete or accelerate the melting.

The material from which the stent is formed is preferably biologically compatible with the fluid which normally flows through the interior of the vessel. One advantageous method of obtaining an integral solid of material for the stent is to obtain the natural fluid which normally flows through the vessel and form it or a derivative of it into the integral solid. For example, if the vessel is a vein or an artery, the stent 10 may be formed from forzen blood plasma taken from the blood which flows through the vessel. Synthetic substitutes for natural fluids could also be used. Once the stent dissoles by melting, the material from which the stent was formed naturally integrates with the fluid flowing through the vessel. Potential problems of adverse tissue reaction and tissue rejection of foreign substances are thereby avoided.

Because of the retaining and aligning capabilities of the stent, the amount of time to complete the anastomosis is reduced. For example in thermal bonding techniques, the use of the stent can eliminate the necessity for taking the three stay sutures to align the vessels prior to thermal bonding. In other types of anastomosis techniques, it may be possible to dispense with the use of stay sutures altogether, since the rigidity and structural support provided by the stent may be sufficient to proceed immediately to joining the vessels without first taking the stay sutures. In those surgical techniques where anastomosis is accomplished solely by suturing, the suturing may proceed more rapidly because of the structural alignment and support available from the stent.

The stent should provide sufficient thermal mass to resist fully melting until completion of the anastomosis. Thermal mass of the frozen stent can be controlled by controlling the temperature of the stent upon insertion. Lower temperature stents upon insertion will withstand melting for a longer period of time than higher temperature stents. Changing the mass or size of the frozen stent also controls its thermal mass. Holes or other structural configurations may be employed in the stent to selectively vary its thermal mass. For example, forming an axially extending opening through the center of the stent will result in less thermal mass and in more rapid melting of the stent, while providing an almost instantaneous passage for fluid through the stent immediately after completion of the anastomosis.

Frozen fluid stents may be prepared by various techniques. For example, a cold temperature-regulated metal slab of large thermal mass and good thermal conductivity could be formed with grooves of various lengths and diameters or cross-sections. These grooves would act as molds into which the fluid would be formed to freeze it into stents of the various sizes. Forceps or other special stent handling devices could be stored at low temperatures so as to maintain the thermal mass of the stent when it is picked up and inserted into the open ends of the vessel.

Another method of using and forming the frozen fluid stents is to place the fluid into a two-part capsule similar to those used to dispense pharmaceuticals. The entire capsule is then cooled to the desired temperature, freezing the fluid into a solid mass. The capsules and enclosed stents are immersed in a cold bath of liquid to maintain the desired temperature until use. The material of the capsule is of low thermal conductivity, thereby thermally insulating the solid stent within its interior until the stent is removed for use. The insulation provided by capsule material allows the surgeon an opportunity to select and size the different stents by handling the capsules without substantially increasing the stent temperature prior to use. When sued, the two parts of the capsule would be separated and the frozen stent removed immediately and inserted into the open ends of the vessel. A variety of sizes of stents could be derived by using capsules of different internal dimensions.

The stent of the present invention offers substantial advantages in anastomosis procedures where the ends of the vessel are joined by a surgical procedure involving thermal bonding. One known thermal bonding technique of anastomosis is the application of a laser beam to the abutted ends of the vessel. As has been previously explained, the prior art technique of anastomosis by laser beams has required the use of three stay sutures at approximately 120 degree circumferential intervals to hold the ends of the vessel in abutment before the laser beam can be applied to seal the ends together. As shown in FIG. 2, the size of the stent 10 is sufficient to hold the vessel ends in aligned abutment, thereby allowing the almost immediate application of a beam 22 from a laser 24 directly to the junction at the ends 18 and 20 of the vessel portions 14 and 16. Anastomosis by thermal bonding will proceed very rapidly since the thermal bonding technique consumes very little time, compared to suturing.

One particular advantage and improvement offered by the use of a frozen fluid stent in anastomosis procedures by thermal bonding is that the cool thermal mass of the stent protects the important inner coat or tuncia intima of the vessel from destruction due to the heat generated by the thermal bonding beam. In prior techniques of anastomosis employing thermal bonding, the tuncia intima was virtually unprotected. Heat energy applied from the beam could destroy the tuncia intima, or damage it to inhibit natural growth after anastomosis or to initiate thrombosis in the blood and thereby cause a clot to occlude the vessel. The thermal mass of the present stent at the interior of the vessel may also inhibit the unintentional perforation of the vessel by the thermal bonding beam, as a result of a more uniform and consistent thermal mass or reservoir against which to regulate the power of the thermal bonding beam. Another substantial advantage and improvement is the elimination of the stay sutures. Of course, taking the stay sutures in the ends of the vessel portions to be joined involves perforating the vessel portions for insertion of the sutures. The suture perforations add to the risk of fluid leakage from the vessel portions after anastomosis. Use of the stent of the present invention in conjunction with a thermal bonding technique can result in rapid, substantially fluid tight anastomosis of the vessel ends.

Preferred embodiments of the present invention have been shown and described with a degree of particularity. It should be understood, however, that the present disclosure has been made by way of preferred example. The invention itself is defined by the scope of the appended claims.

The invention claimed is:

1. A stent for insertion into the interior of the ends of a tubular vessel in a living being to align the ends of the vessel and support the vessel during anastomosis, comprising an integral solid of a biological fluid material adapted to melt into a fluid which is biologically compatible and naturally integrable with that fluid which normally flows through the vessel, said stent having a predetermined temperature substantially less than the temperature of the vessel upon insertion into the vessel.

2. A stent as defined in claim 1 wherein the biological fluid material comprises frozen blood plasma and the tubular vessel is part of an artery or a vein.

3. A stent as defined in claim 2 wherein the solid is substantially impervious to the conduction of fluid through the vessel when inserted into the interior of the ends of the vessel.

4. A stent as defined in claim 1 wherein the biological fluid material is a frozen fluid and the fluid comprises a blood fluid.

5. A stent as defined in claim 4 wherein the solid is substantially impervious to the conduction of fluid through the interior of the ends of the vessel upon insertion therein.

6. A stent as defined in claim 1 wherein the biological fluid material consists essentially of a blood plasma.

7. A stent as defined in claim 6 wherein the solid is substantially impervious to the conduction of fluid through the interior of the ends of the vessel upon insertion therein.

8. A stent for use in anastomosis of a tubular vessel in a living being, which is adapted to be inserted in the ends of the vessel to align and hold the ends in an abutting relationship during a surgical procedure connecting the ends, and which comprises an integral frozen solid of a biological fluid material, the frozen solid having a predetermined thermal mass which fully melts after completion of the surgical procedure.

9. A stent as defined in claim 8 wherein the solid biological fluid comprises a frozen blood fluid.

10. A stent as defined in claim 9 wherein the blood fluid comprises blood plasma.

11. A stent as defined in claim 8 in which the integral solid is substantially impervious to the flow of fluid through the interior of the vessel upon insertion into the ends of the vessel.

12. A stent for insertion into the interior of the ends of a turublar vessel in a living being to align the ends of the vessel and support the vessel during anastomosis. comprising an integral solid of a biological fluid material adapted to melt from the solid into a fluid, the biologically compatible material being compatible with that fluid which normally flows through the vessel, said stent having a predeterined temperature substantially less than the temperature of the vessel upon insertion into the vessel and which is sufficiently low to maintain the temperature of the stent less than the normal temperature of the vessel until anastomosis is completed.

13. A stent as defined in claim 12 wherein the biological fluid material is a frozen fluid which comprises a blood fluid.

14. A stent as defined in claim 13 wherein the blood fluid comprises frozen blood plasma and the tubular vessel is part of an artery or a vein.

15. A stent for use in anastomosis of a tubular vessel in a living being, which is adapted to be inserted in the ends of the vessel to align and hold the ends in an abutting relationship during a surgical procedure connecting the ends, and which comprises an integral solid of a biological fluid material which fully melts after completion of the surgical procedure into the fluid flowing through the vessel in response to body heat of the living being, said integral solid being substantially impervious to the conduction of fluid through the interior of the vessel upon insertion of the stent into the ends of the vessel.

16. A stent as defined in claim 15 wherein the integral solid of biological fluid material comprises a frozen blood fluid.

17. A stent as defined in claim 16 wherein the frozen blood fluid comprise a blood plasma.

* * * * *